United States Patent [19]

Lien

[11] Patent Number: 4,634,714

[45] Date of Patent: Jan. 6, 1987

[54] INHIBITION OF PROLACTIN RELEASE BY A BENZODIOXINYLIMIDAZOLINE DERIVATIVE

[75] Inventor: Eric L. Lien, Paoli, Pa.

[73] Assignee: American Home Products Corporation, New York, N.Y.

[21] Appl. No.: 557,084

[22] Filed: Dec. 1, 1983

[51] Int. Cl.⁴ .......................................... A61K 31/415
[52] U.S. Cl. ................................................... 514/397
[58] Field of Search ...................... 424/273 R; 514/397

[56] References Cited

U.S. PATENT DOCUMENTS

| 4,302,469 | 11/1981 | Kluge et al. | 424/273 R |
| 4,315,021 | 2/1982 | Kluge et al. | 424/273 R |
| 4,397,860 | 8/1983 | Chapleo et al. | 424/273 R |
| 4,402,967 | 9/1983 | Waterbury | 424/273 R |

FOREIGN PATENT DOCUMENTS 2068376 8/1981 United Kingdom .................... 407/4

OTHER PUBLICATIONS

Physician's Desk Reference, "Parlodel®" pp. 1748–1749 (1984).
Parkes, N. Eng. J. Med., 301, 873 (1979).
Caroon et al., J. Med. Chem., 25, 666 (1982).
Meltzer et al., J. Pharm. Exp. Ther., 224, 21 (1983).

*Primary Examiner*—Stanley J. Friedman
*Attorney, Agent, or Firm*—Richard K. Jackson

[57] ABSTRACT

2-(2,3-Dihydro-1,4-benzodioxin-2-yl)-4,5-dihydro-1H-imidazole, or a pharmaceutically acceptable salt thereof, is useful in the treatment of hyperprolactinemic states in warm-blooded animals.

2 Claims, No Drawings

INHIBITION OF PROLACTIN RELEASE BY A BENZODIOXINYLIMIDAZOLINE DERIVATIVE

This invention relates to the use of 2-(2,3-dihydro-1,4-benzodioxin-2-yl)-4,5-dihydro-1H-imidazole, or a pharmaceutically acceptable salt thereof, for inhibition of prolactin release in the treatment of conditions requiring the regulation of the release of this hormone.

Prolactin is an important pituitary hormone whose physiological functions include the promotion of mammary gland development and the induction of lactation. Prolactin secretion is regulated by the thyrotropin releasing factor (thyroliberin or TRH) and dopamine which are secreted by the hypothalamus. It is known that the administration of various substances will stimulate prolactin release: for example, the narcotic-analgesic morphine, the endogenous brain analgesic peptide methionine-enkephalin, and certain methionine-enkephalin analogs, have been demonstrated to effect release of prolactin. It is also known that certain substances will inhibit prolactin release, for example, the narcotic antagonist naloxone inhibits prolactin release [see C. Shaar et al., Fed. Proc., 36, 311 (1977)] as does bromocriptine [D. Parkes, N. Eng. J. Med., 301, 873, (1979)]. Inhibition of prolactin release is useful in the treatment of those conditions where excessive prolactin levels are undesirable, as for example in the treatment of galactorrhea and infertility due to hyperprolactinemia.

This invention is directed to a method for inhibiting prolactin release in warm-blooded animals which comprises administering to such a warm-blooded animal an effective amount of 2-(2,3-dihydro-1,4-benzodioxin-2-yl)-4,5-dihydro-1H-imidazole or a pharmacologically acceptable acid addition salt thereof.

The compound employed in the process of this invention is a known α-2 adrenergic antagonist [J. Carson et al., J. Med. Chem., 25, 666, (1972)].

In carrying out the method of this invention the active compound can be administered either alone or in combination with inert pharmaceutically acceptable carriers in a variety of dosage forms, orally or parenterally. The dose requirements will vary with the severity of the conditions being presented, the animal being treated, or the dosage form employed. Therapy is instituted at low dosages and the dosage is increased incrementally until the desired prolactin-inhibiting effect is achieved.

Prolactin in blood samples can be determined by the specific double antibody radioimmunoassay method of Neill and Reichert, Endocrinology, 88, 548 (1971).

With large animals (about 70 kg. body weight), by the parenteral route, such as by intramuscular or subcutaneous injection an effective dose is from about 10 mg to about 1 gm., preferably about 25 mg. to about 200 mg.

For unit dosages, the active compound can be compounded into any of the usual oral or parenteral dosage forms, including tablets, capsules, elixir, or suspensions. The dosage forms can contain conventional inert pharmaceutical carriers as diluents, lubricating agents, stabilizing agents, preserving agents, or flavoring agents, as needed. Suitable pharmaceutical carrying agents and methods of preparation thereof will be apparent to those skilled in the art. In all cases, the proportions of the active ingredient in a dosage form must be sufficient to impart prolactin inhibiting activity thereto.

The ability of 2-(2,3-dihydro-1,4-benzodioxin-2-yl)-4,5-dihydro-1H-imidazole and its pharmaceutically acceptable salts to inhibit prolactin release has been demonstrated in rats as described in the following Examples.

EXAMPLE 1

Male Charles River CD rats, at about 300 grams in weight, received saline, yohimbine (the standard α-2 adrenergic antagonist) or 2-(2,3-dihydro-1,4-benzodioxin-2-yl)-4,5-dihdyro-1H-imidazole hydrochloride (test compound) subcutaneously. Sixty minutes later the rats were decapitated and trunk blood collected in Traysylol-EDTA (12 mg. EDTA in 6000 units Traysylol). Each plasma sample is assayed for prolactin in triplicate by specific double antibody radioimmunoassay using NIAMDD reagents. Prolactin is determined by the method of Neill and Reichert, Endocrinology, 84, 548 (1971). The results are shown in the table below:

| Treatment | Dose mg/kg | Plasma Prolactin ng/ml |
|---|---|---|
| Saline | — | 4 ± 1 |
| Test compound | 0.1 | 11 ± 6 |
|  | 1.0 | 3 ± 0.9 |
|  | 10.0 | 2 ± 0.4+ |
| Yohimbine | 0.1 | 6 ± 1 |
|  | 1.0 | 28 ± 6+ |
|  | 10.0 | 45 ± 5++ |

+$p < 0.05$ vs. saline
++$p < 0.01$ vs saline

EXAMPLE 2

Male Charles River CD rats, about 300 grams in weight, received saline or 2-(2,3-dihydro-benzodioxin-2-yl)-4,5-dihydro-1H-imidazole hydrochloride (test compound) subcutaneously 60 minutes before sacrifice. Morphine (10 mg/kg, s.c.) or saline was injected 30 minutes before sacrifice as a means of stimulating plasma prolactin levels.

| Treatment 1 | Treatment 2 | Plasma Prolactin ng/ml |
|---|---|---|
| Saline | Saline | 12 ± 2 |
| Saline | Morphine | 54 ± 7 |
| Test Compound 0.1 mg/kg | Morphine | 61 ± 14 |
| Test Compound 0.1 mg/kg | Morphine | 45 ± 9 |
| Test Compound 10.0 mg/kg | Morphine | 16 ± 2+ |

+$p < 0.01$ vs. morphine alone.

The results of Example 1 show that 2-(2,3-dihydro-1,4-benzodioxin-2-yl)-4,5-dihydro-1H-imidazole hydrochloride suppresses basal prolactin levels while the standard α-2 adrenergic antagonist, yohimbine, elevates prolactin levels. Example 2 demonstrates that the test compound is capable of reversing morphine-stimulated prolactin release. Thus, the test compound is capable of lowering plasma prolactin levels under both basal and stimulated conditions in the standard experimental animal.

What is claimed is:

1. A method for lowering blood serum prolactin levels in warm-blooded animals which comprises administering, orally or parenterally, to a warm-blooded animal in need of a lowered serum prolactin level an amount of 2-(2,3-dihydro-1,4-benzodioxin-2-yl)-4,5-dihydro-1H-imidazole, or a pharmaceutically acceptable acid addition salt thereof, sufficient to lower said serum prolactin level.

2. A method for lowering blood serum prolactin levels in a mammal which comprises administering, orally or parenterally, to a mammal in need of a lowered serum prolactin level, an amount of 2-(2,3-dihydro-1,4-benzodioxin-2-yl)-4,5-dihydro-1H-imidazole, or a pharmaceutically acceptable acid addition salt thereof, sufficient to lower said serum prolactin level.

* * * * *